US005174325A

United States Patent [19]

Okel et al.

[11] Patent Number: 5,174,325

[45] Date of Patent: Dec. 29, 1992

[54] RETRACTION MECHANISM FOR VALVE INSERTABLE SENSORS

[75] Inventors: Mark C. Okel, Laguna Hills; Barry R. West, Santa Ana, both of Calif.

[73] Assignee: Rosemount Analytical Inc., LaHabra, Calif.

[21] Appl. No.: 883,157

[22] Filed: May 14, 1992

[51] Int. Cl.[5] ........................ G01L 11/00; G01L 19/00

[52] U.S. Cl. .................................... 137/317; 73/866.5

[58] Field of Search ................ 137/315, 317; 73/866.5

[56] References Cited

U.S. PATENT DOCUMENTS

| | | | |
|---|---|---|---|
| 2,805,273 | 9/1957 | Cuthbert | 137/317 |
| 3,007,340 | 11/1961 | Kraftson | 73/866.5 |
| 3,576,195 | 4/1971 | Richard, Jr. | 137/317 |
| 3,829,761 | 8/1974 | Shimizu et al. | 324/30 B |
| 3,830,480 | 8/1974 | Grant | 73/866.5 |
| 3,983,756 | 10/1976 | Danguillier et al. | 137/317 |
| 4,096,754 | 6/1978 | Beveridge, Jr. et al. | 137/317 |
| 4,633,713 | 1/1987 | Mesnard et al. | 73/866.5 |
| 4,640,128 | 2/1987 | Lewis | 73/866.5 |
| 4,697,465 | 10/1987 | Evans et al. | 73/866.5 |
| 4,742,717 | 5/1988 | Ichino | 73/866.5 |
| 4,866,998 | 9/1989 | Stewart et al. | 73/866.5 |

OTHER PUBLICATIONS

Brochure of Ingold Electronics Inc.: Insertion Probe 768-35 (p. 17) and Insertion Probe 769-35 (p. 18).

Brochure of Electro-Chemical Devices, Inc.: Insertion/Submersion pH Sensor, Model PHS17.

Brochure of Lakewood Instruments, Inc.: Model 520 Series pH/Redox Sensor-Transmitter.

Brochure of Sensor Technology, Inc.: Insertion/Submersion pH Sensor, Model 916.

Brochure of Signet Scientific, Inc.: MK 319 Wet Tap Assembly.

Brochure of Van London Company, Inc.: Mark VII Insertion Sensors.

Instruction Manual of Rosemount Analytical: Model 140, 141 and 142 Conductivity Sensor Assemblies.

Brochure of Sensorex, Inc., Bulletin 410: Insertable Flat Surface Combination pH Electrode.

Brochure of Leeds & Northrup Instruments; 7774 Insertion Mounting with Removal Device.

Brochure of TBI: Instruments for Process Monitoring, p. 346, High Pressure Series, Models 471 and 475.

*Primary Examiner*—George L. Walton
*Attorney, Agent, or Firm*—Kinney & Lange

[57] ABSTRACT

A retraction mechanism permits easily removing a sensor assembly from a pressurized process fluid container through a valve attached to an opening in the container. The retraction mechanism includes a folding support linkage having a first end and a second end formed from at least two links that are joined together to have a pivot joint located therebetween. The first end of the support linkage is joined to the sensor assembly, while the second end of the support linkage is joined to the valve or the fluid container. The two links are partially folded when the sensor assembly is in operable position, and pivot about the pivot joint to unfold when the sensor assembly is removed. The retraction mechanism further includes a damper connected between the two links of the support linkage. The damper provides a damping or restraining force for the sensor assembly as the sensor assembly is removed from the fluid container.

15 Claims, 3 Drawing Sheets

40
48
57
66
62
56
70
74
64
54
72
58
52
42
59
60
20
22
16
80
10
76
30
19
24
23
14
12

RETRACTION MECHANISM FOR VALVE INSERTABLE SENSORS

BACKGROUND OF THE INVENTION

The present invention relates to a retraction mechanism to remove a sensor assembly extending through a valve into a process fluid container from the process fluid container More particularly, the present invention provides a sensor retraction mechanism having a support linkage connected between the sensor assembly and the process fluid container with a damper to prevent uncontrolled ejection of the sensor assembly from the container when the container is under fluid pressure.

In order to measure properties of a fluid, such as conductivity, pH or temperature, a sensor usually must be placed in contact with the process fluid. The fluid can reside either in a process line or within a process container. Under most circumstances, the fluid is under pressure. It is sometimes desirable to install or remove the sensor without relieving the pressure of the process fluid. Typically, this procedure involves using a sensor assembly having a sensing element mounted on a long tube that extends through a gate or ball valve body connected to the fluid container. When the sensing element must be calibrated, replaced, inspected or cleaned, the tube and the sensing element as a unitare retracted through the gate or ball valve body until the end of the sensor assembly clears the valve element in the valve body. Then, the valve can be closed to keep the fluid under pressure, while the sensor assembly is removed completely from the valve to allow proper servicing.

If the sensor assembly is under pressure from the process fluid in the container, then when the sensor assembly is unlocked from the valve body, the sensor assembly is subjected to a force that tends to expel it from the valve body. Cables, chains, or lanyards have been connected to the sensor assembly to prevent the sensor assembly from accidentally ejecting from the valve body. Stop rings or flanges located near the end of the sensor assembly that contact opposed flanges or a tube fitting have also been used in an attempt to prevent the end of the sensor assembly from ejecting from the valve body.

SUMMARY OF THE INVENTION

The present invention relates to a sensor retraction mechanism for permitting removal of a sensor assembly from a pressurized process fluid container or line through a valve opening into the container and through which the sensor assembly is inserted. The retraction mechanism includes a support linkage that has few parts which move when the sensor assembly is inserted or removed and such movement is controlled. As disclosed, the linkage has a first end and a second end formed from at least two links that are joined together at a pivot joint. The first end of the linkage is pivotally joined to the sensor assembly, while the second end of the linkage is pivotally joined to a stationary point relative to the fluid container. The two links pivot about the pivot joints to fold when the sensor assembly is installed and unfold when the sensor assembly is removed. The retraction mechanism further includes a damper connected between two links of the linkage. The damper provides a damping or restraining force that resists rapid outward movement of the sensor assembly from the fluid container.

In the preferred embodiment, the retraction mechanism includes a limiter or stop device to limit outward displacement of the sensor assembly from the valve to a preselected position. At this position, a pressure seal remains effective between the sensor assembly and the valve, but the valve can be closed to close the opening in the container or line. After closing the valve, the sensor assembly can be removed from the valve for servicing.

The limiter can include a positive stop, such as a radial protrusion that contacts an opposed stop surface on a tube fitting or, alternatively, a control link connected to the linkage. When embodied as a control link, the limiter mounts between two links that are on opposite sides of the pivot joint. The control link has a longitudinal guide slot through which a stop pin member mounted to one of the support links slides therewithin. Contact of the stop pin member with end surfaces of the longitudinal guide slot stops or limits outward displacement of the sensor assembly at the selected position.

In a further preferred embodiment, the control link includes a second longitudinal guide slot extending from an end of the first mentioned longitudinal guide slot, and having a slot width narrower than the first longitudinal guide slot. In addition, the stop pin member includes a first portion that has a width slidable in the first longitudinal guide slot but not slidable in the second longitudinal guide slot, and a second smaller width portion that will slide in the second longitudinal guide slot. The stop pin member is selectively positionable either with the first portion aligned and slidable in the first longitudinal guide slot or with the second portion aligned with the second longitudinal guide slot for sliding in the second longitudinal guide slot. The length of the longitudinal guide slot allows the sensor assembly to displace outwardly from the valve body a sufficient distance such that the valve can be closed, thus sealing the pressurized container. The length of the second longitudinal guide slot allows the sensor assembly to be removed from the tube fitting without disconnecting the control link.

DETAILED DESCRIPTION OF THE PREFERRED EMBODIMENTS

Figures 1, 4:
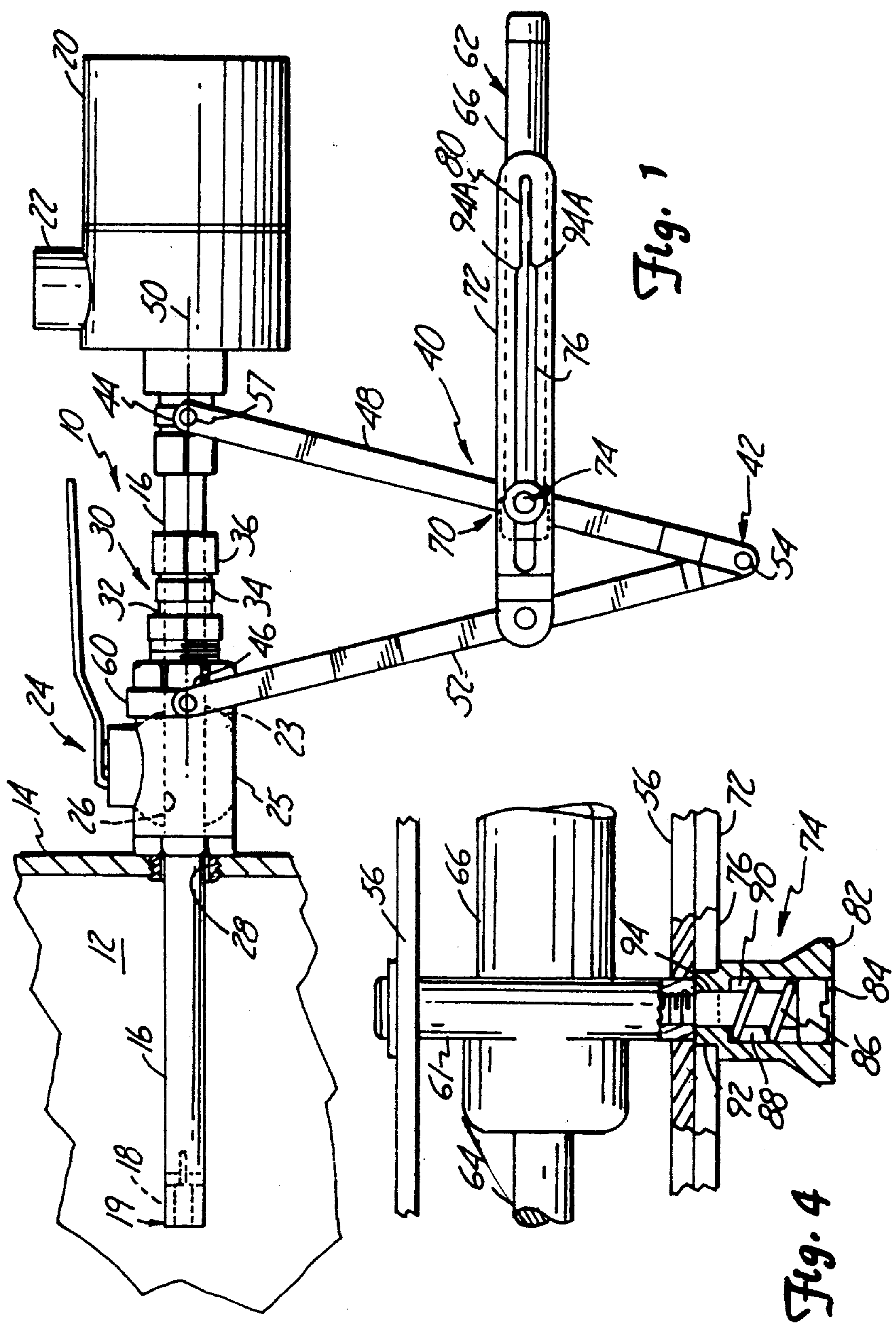
FIG. 1 is a side elevational view of a first embodiment of a retraction mechanism of the present invention illustrated with a sensor assembly in an inserted, operable position.
FIG. 4 is a sectional view of a movement limiter or a stop pin member.

A sensor assembly 10 as shown for measuring properties of a liquid 12 is illustrated in FIG. 1. A tube end 19 of the sensor assembly 10 is located in the liquid 12 which is enclosed in a suitable fluid container 14 such as a tank or pipe for use in an industrial process. The sensor assembly 10 comprises a sensor housing tube 16 and a sensing element 18 carried by the tube end 19 of the sensor housing tube 16. The sensing element 18 provides signals representative of the desired fluid properties. A junction box enclosure 20 mounted on the end of the sensor housing tube 16 opposite the sensing element 18 receives signal leads from the sensing element 18 through the sensor housing tube 18. Signal lines, not shown, connect to the signal leads and extend through a conduit connection 22 to an analysis station, not shown.

Figures 2, 3:
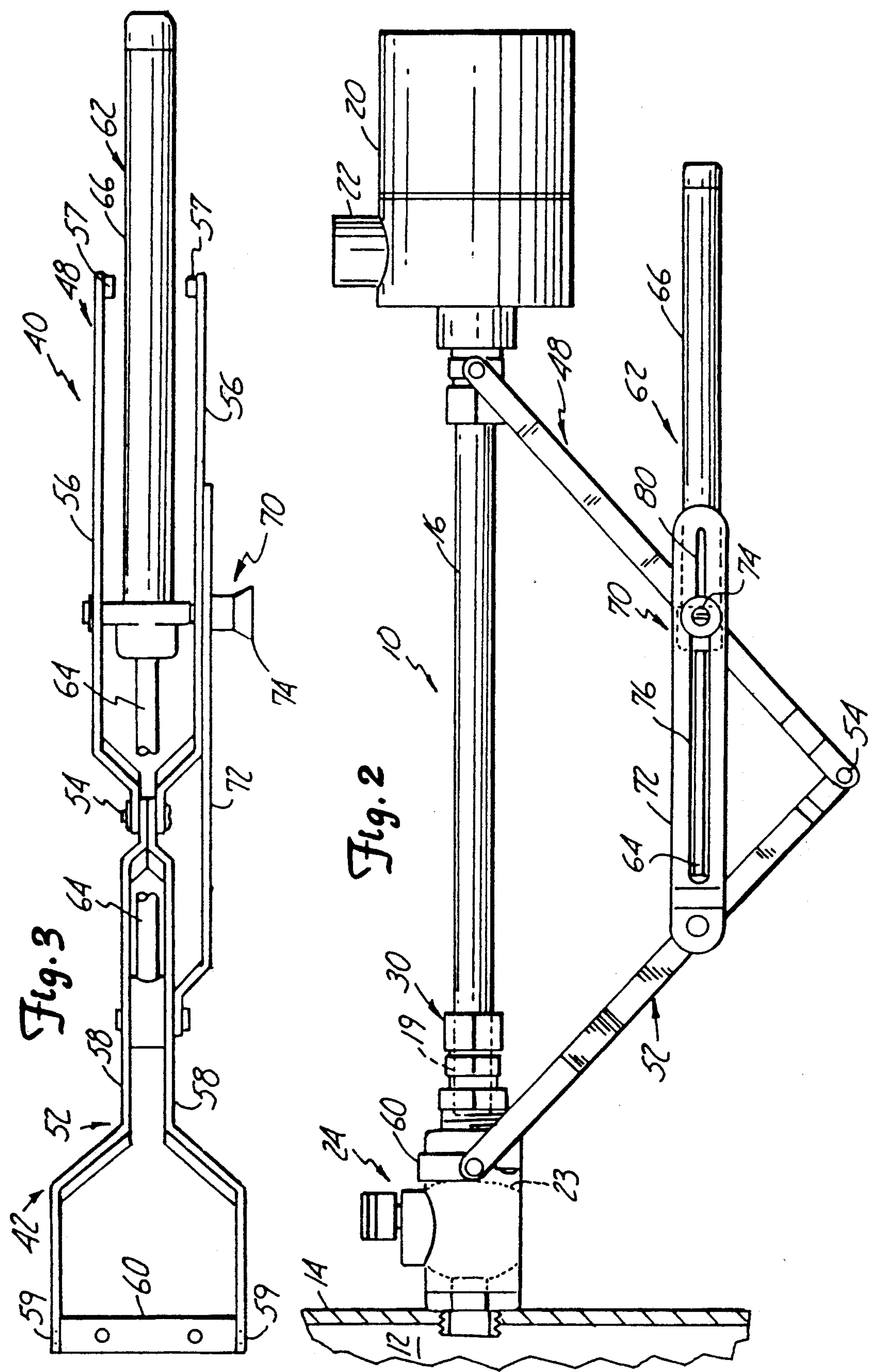
FIG. 2 is a side elevational view of the retraction mechanism of FIG. 1 illustrated with the sensor assembly in a partially retracted position.
FIG. 3 is a top view of the retraction mechanism of FIG. 2 with a portion of a damping rod removed.

The sensor assembly 10 is mounted within the container 14 through a valve 24. This method of mounting a sensor assembly is well known, and thus, a brief description will suffice. The valve 24 has an valve body 25 which sealingly attaches to a fitting on the fluid container 14 at a opening 28 and as shown, includes a ball 23 having a through bore or port 26 with an inner diameter slightly larger than the outer diameter of the sensor housing tube 16. Port 26 aligns with similar size bores in the end of valve body 25 with the valve in an open position. O-rings, not shown, are disposed in suitable grooves in end bores to seal on sensor housing tube 16 when the sensor housing tube 16 is inserted. When the sensor assembly 10 is removed from the port 26, and clears ball 23, the ball 23 can be selectively rotated about an axis perpendicular to the axis of port 26 to seal off the opening 28, as schematically illustrated in FIG. 2.

Figures 5, 6:
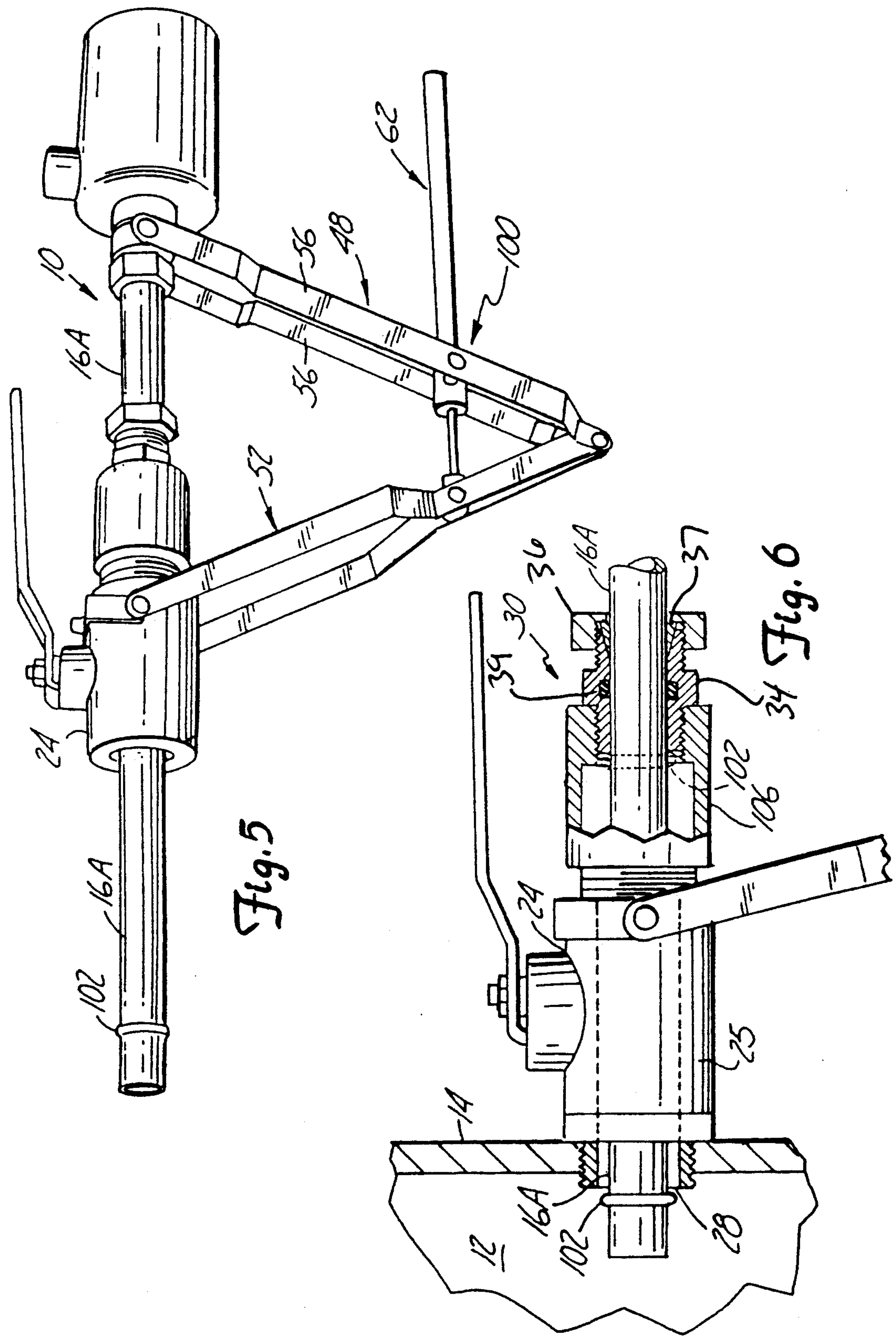
FIG. 5 is a perspective view of a second embodiment of a retraction mechanism of the present invention illustrated with a sensor assembly in an operable position.
FIG. 6 is a partial, sectional view of the retraction mechanism of FIG. 5 mounted to a fluid container.

A compression fitting 30 is threadably joined to the valve 24 on an end 32. The compression fitting 30 releasably secures the sensor housing tube 16 to the valve body 25 and provides a restraining force that is sufficient to prevent outward displacement of the sensor assembly 10 when the container 14 is pressurized. In the embodiment illustrated, the compression fitting 30 includes a compression fitting body 34 threadably joined to a bore in the valve body 25 of valve 24. The compression fitting body 34 has a male portion on which a compression nut 36 is threaded. Referring to FIG. 6, the compression fitting 30 is shown in section. A ferrule 37 on the interior of the compression fitting body 34 is compressed onto the sensor housing tube thereby gripping the sensor housing tube to prevent outward displacement. Fittings sold by Swageloc Co. of Solon, Ohio, U.S.A. are suitable.

Other types of tube fittings that selectively secure the sensor housing tube 16 to the valve 24 can be used. For example, a conventional union tube fitting can be used as long as the fitting is sealed to prevent pressure leaks. Instead of a compression ferrule, nut 36 could have a flange which contacts a radial protrusion on the sensor housing tube 16. When the nut is threaded onto a first connecter, contact between the ring on the sensor housing tube 16 and the flange of the nut prevents outward displacement of the sensor assembly 10.

Removing the sensor assembly 10 from a pressurized fluid container 14 can result in the uncontrolled ejection of the sensor assembly 10 from the valve body 25 if the nut 36 is loosened. A sensor retraction mechanism of the present invention indicated generally at 40 in FIGS. 1-3 prevents uncontrolled ejection of the sensor assembly 10 from the valve body 25. The sensor retraction mechanism 40 dampens or restrains movement of the sensor assembly 10 as it moves outwardly through the valve body 25.

The sensor retraction mechanism 40 includes a support or scissor linkage 42 having a first end 44 and a second end 46. The first end 44 is pivotally joined to the sensor assembly 10 at an end opposite the sensing element 18. The second end 46 of the linkage 42 is pivotally joined to a stationary point relative to the fluid container 14 such as on the valve body 25. As illustrated in FIG. 3, the linkage 42 includes two relatively movable members, namely, a first support link or sensor link 48 formed from a pair of spaced, coextensive members 56,56 that are pivotally joined to the sensor assembly 10 with pivot pin connections 57,57. As illustrated in FIG. 1, the ends of members 56,56 straddle the sensor assembly 10 and the pivot connections 57,57 and are substantially on line with a longitudinal axis 50 of the sensor housing tube 16. The pivot connections 57,57 are fixed to the sensor assembly 10.

Referring back to FIG. 3, the linkage 42 further includes a second support link or valve link 52 pivotally joined to the first support link 48 at an end opposite the sensor assembly 10 to form a pivot joint 54. The second support link 52 is formed from a pair of members 58,58 that are spaced apart at ends opposite pivot joint 54 and are pivotally joined to depending legs of a saddle bracket 60 with pivot connections 59,59. Saddle bracket 60 is attached to the valve body 25, the legs of the saddle bracket 60 straddle the valve body and locate pivot connection 59,59 to be aligned with the axis 50 of sensor housing tube 16. The link 52 and bracket 60 further secure the sensor retraction mechanism 40 to the valve 24.

A damper 62 connects between the links 48 and 52 at a location spaced from pivot joint 54 and provides a damping or retraining force to the sensor assembly 10 as it moves outwardly from the container 14 through the valve body 25 when the compression nut 36 is loosened and the links 48 and 52 unfold. In the embodiment as illustrated in FIG. 3, a fluidic damper is used. Damper 62 has a rod 64 that has a connected piston or movement resisting member within a fluid containing housing 66. The rod 64 is joined to the link 52, between members 58,58, and the fluid containing housing 66 is joined to the link 48 between members 56,56, using a support collar 61, illustrated in FIG. 4. Preferably, the damper 62 provides a continuous resistive force only to movement of the sensor assembly 10 out of the valve 24. In other words, the damper 62 allows the sensor assembly 1? to be easily inserted through the valve 24 and into the fluid container 14 by offering substantially less resistive force for insertion than the damping force present during removal of the sensor assembly 10 from the valve 24. Although a hydraulic damper is preferred, other dampers using pneumatic damping or other means for dissipating the kinetic energy of the sensor assembly can be used.

The sensor retraction mechanism 10 further includes a limiter 70 to limit or stop outward displacement of the sensor assembly 10. The sensor assembly 10 is stopped in order that the valve 24 can be closed to seal the opening 28 after the sensor housing tube 16 clears the ball 23 and while the end of the sensor assembly 10 remains in the compression fitting 30. As shown in FIG. 6, the compression fitting 30 includes an 0-ring 39 to prevent fluid leakage. Closing the valve 24 seals the opening 28. The limiter 70, stops outward displacement of the sensor assembly 10 by limiting angular or pivotal displacement of the links 48 and 52 on the pivot joint 54.

In the embodiment illustrated in FIGS. 1-4, the limiter 70 comprises a control or stop link 72 joined to the linkage 42 and a stop pin member 74 that is slidable within a longitudinal slot 76 of the control link 72. The control link 72 is pivotally attached to the link 52 at a location spaced from pivot joint 54. The stop pin member 74 is threadably supported on an end of the support collar 61 for damper 62 through one of the members 56 of link 48. The stop pin member 74 passes through the longitudinal guide slot 76 which allows the stop pin member 74 to slide a limited distance along the control link 72. The distance that the stop pin member 74 can slide is the distance necessary for the end of the sensor assembly 10 to clear port 26 in the ball 23 of the valve 24. This limited distance allows the ball 23 of valve 24 to be closed and seal the container opening 28 while the tube end 19 of the sensor assembly 10 remains in the compression fitting 30, as illustrated in FIG. 2.

With the opening 28 sealed, the tube end 19 of the sensor housing tube 16 is removed from the compression fitting 30 by allowing the sensor assembly 10 to move outwardly past the compression fitting 30. Referring to FIGS. 1 and 2, the control link 72 includes a second longitudinal guide slot 80 that extends generally parallel to the longitudinal guide slot 76 from an end thereof. The second longitudinal guide slot 80 is narrower than the longitudinal guide slot 76. The stop pin member 74 is selectively positionable to slide only in the longitudinal guide slot 76 or, after manual release, slide in the second longitudinal guide slot 80.

The stop pin member 74 is illustrated in detail in FIG. 4. A knob portion 82 is positionable relative to a shouldered cap screw 84 to control when the stop pin member can slide in slot 80. The cap screw 84 is threaded into the support collar 61 and acts as a stud. The knob portion 82 fits over the cap screw 84. A helical spring 86 located in a cylindrical cavity 88 of the knob portion 82, between an inner annular flange 90 on the knob portion 82 and the head of the cap screw 84, biases the knob portion 82 such that an end portion 92 is abutted against the outer surface of one member 56 and is positioned within the longitudinal guide slot 76. The end portion 92 slides along the longitudinal guide slot 76 but is too large in diameter to enter or slide in the second longitudinal guide slot 80. When the end portion 92 contacts slot end surfaces 94A(FIG. 1) of the longitudinal guide slot 76, where slot 76 joins the second longitudinal guide slot 80, unfolding movement of the linkage 42 and axial outward movement of sensor assembly 10 is stopped with the tube end 19 of sensor housing tube 16 remaining in the compression fitting 30, as illustrated in FIG. 2. The knob portion 82 is then pulled outwardly against the spring force from spring 86 along the longitudinal axis of the cap screw 84 to remove end portion 92 from slot 76 so it clears the control link 72 to expose a shaft portion 94 of the cap screw 84. The shaft portion 94 has a diameter slightly smaller than the width of the second longitudinal slot 80 and will slide in slot 80. After the valve 24 is closed, continued outward displacement of the end tube 19 out of the compression fitting 30 with the linkage 42 unfolding about pivot joint 54 is then possible.

Removal of an inserted sensor assembly 10 is as follows. With the ball 23 of the valve 24 open allowing the sensor housing tube 16 of sensor assembly 10 to project therethrough into the fluid container 14, the compression fitting 30 is loosened. The damper 62 prevents rapid ejection of the sensor assembly 10 by providing a damping or restraining force to outward movement of the sensor housing tube 16 of the sensor assembly 10. Outward displacement of the sensor assembly 10 continues with pivotal unfolding movement between the links 48 and 52 about the pivot joint connection 54 until the end portion 92 of stop pin member 74 contacts the end surfaces 94A of the longitudinal guide slot 76. At this position, the sensor housing tube 16 clears ball 23 so it is closed to seal the opening 28. The knob portion 82 is then pulled outwardly to release the end portion 92 from slot 76 and align the shaft portion 94 with the second longitudinal guide slot 80 on control link 72. The sensor assembly 10 can then be pulled outwardly from the compression fitting 30 with the links 48 and 52 continuing unfolding, relative pivotal movement about the pivot joint connection 54 and the shaft portion 94 sliding within the second longitudinal slot 80. When the sensor housing tube 16 clears the nut 36, the sensor assembly 10 can pivot on pivot connections 57,57 or 59,59, allowing the sensing element 18 to be serviced or replaced as required without further disassembly of the sensor retraction mechanism 40.

Installation of the sensor assembly 10 into the fluid container 14 using the sensor retraction mechanism 40 is reversed with respect to removal and generally is as follows. The sensor assembly 10 is inserted through the loosened compression fitting 30 and into the valve body 25, as illustrated in FIG. 2. The ball 23 is then rotated to align the port 26 with end bore portions of body 25 and open the opening 28. O-rings 39 in the compression fitting 30 contacts the sensor housing tube to prevent the fluid 12 from discharging. The sensor housing tube 16 of sensor assembly 10 is then inserted through the port 26 and through opening 28 into the fluid container 14 to the position illustrated in FIG. 1. The compression nut 36 of compression fitting 30 is then tightened to secure the sensor assembly 10 in place. Besides allowing simple insertion of the sensor assembly 10, the sensor retraction mechanism 40 is automatically in position for subsequent removal of the sensor assembly 10. The knob portion 82 snaps into place with the end portion 92 in slot 76 as the linkage 42 folds.

A second embodiment of the retraction mechanism of the present invention is illustrated in FIG. 5 at 100. Like the retraction mechanism 40, the link 48 of the retraction mechanism 100 connects to the sensor assembly 10, while the link 52 connects to the valve 24. The links 48 and 52 are joined together at the pivot connection 54 with the damper 62 connected between the links 48 and 52, providing a damping force for outward displacement of the sensor assembly 10 from the valve 24. However, the retraction mechanism 100 differs from the retraction mechanism 40 in that outward displacement of the sensor assembly 10 is stopped by a radial protrusion 102 on a sensor housing tube 16A, which is identical to tube 16 except for the radial protrusion 102.

Referring to FIG. 6, the radial protrusion 102 is located on the sensor housing tube 16A a selected distance from the end of the sensor assembly 10 so that the valve 24 can be closed when initial outward movement of the sensor assembly 10 is stopped. Specifically, when the compression fitting 30 is released from the sensor housing tube 16, the sensor assembly 10 moves outwardly through the valve 24 until the protrusion 102 contacts the compression fitting 30. A coupling 106 is threaded onto the end of valve body 25 between the valve body 25 and the compression fitting 30. When the end portion of the sensor housing tube 16A of sensor assembly 10 is located within the coupling 106, the valve 24 can be closed to seal the opening 28. By unthreading the coupling 106 from the valve 24, the sensor assembly 10 can be pivoted to allow servicing or replacement of the sensing element contained therein. Although a radial protrusion 102 is included in this embodiment, the retraction mechanism 100 differs from known retraction mechanisms because the damper 62 provides a continuous damping force to outward movement of the sensor assembly 10, rather than relying upon the radial protrusion to provide a quick, sudden stop.

In summary, the present invention provides an improved retraction mechanism for valve insertable sensor assemblies. The retraction mechanism controls ejection of the sensor assembly from a process container by providing a continuous damping force to the sensor assembly. The retraction mechanism is formed from a simple two-piece linkage with a damper connected between the relatively movable links. In addition, the retraction mechanism is unobtrusive in that the sensor can be serviced or replaced by disconnecting only a minimal amount of the retraction mechanism assembly, thereby insuring that when the assembly is reinserted within the container, the retraction mechanism is operable.

It should be noted that a ball valve or a gate valve can be used. The valve and other parts of the sensor assembly 10 are made of material which will withstand the corrosive effects of the fluid 12, if any.

Although the present invention has been described with reference to preferred embodiments, workers skilled in the art will recognize that changes may be made in form and detail without departing from the spirit and scope of the invention.

What is claimed is:

1. An apparatus for permitting removal and installation of a sensor assembly through a valve attached to an opening in a process fluid container, the apparatus comprising:

a support linkage having a first end and a second end formed from at least two links that are joined together for relative movement therebetween the links pivoting about the pivot joint as the sensor assembly is moved relative to the fluid container, the first end of the support linkage joined to the sensor assembly, and the second end of the support linkage mounted relative to the fluid container, wherein the linkage is in a substantially collapsed condition when the sensor assembly is inserted through the valve and into the container and securely mounted relative to the container, and wherein the linkage is in an expanded condition when the sensor assembly is removed from the container and the valve; and damping means for resisting rapid relative movement of the links as the sensor assembly is removed from the container and through the valve as the linkage is expanded so that the valve can be closed to seal the opening.

2. The apparatus of claim 1 wherein the links are joined together to have a pivot joint located therebetween, the links pivoting about the pivot joint as the sensor assembly is moved relative to the fluid container.

3. The apparatus of claim 1 wherein the second end is pivotally mounted to the valve.

4. The apparatus of claim 1 and further including stopping means to stop movement of the sensor assembly away from the valve at a selected position with respect to the valve.

5. The apparatus of claim 4 wherein the stopping means is selectively releasable to allow continued movement of the sensor assembly beyond the selected position.

6. The apparatus of claim 5 wherein the stopping means comprises a control link having a longitudinal guide slot, and a stop member slidable in the longitudinal guide slot for a limited distance, wherein an end of the control link is joined to one of the links and the stop member is mounted to the other of the two links.

7. The apparatus of claim 6 wherein the control link includes a second longitudinal guide slot, providing an extension of the first mentioned longitudinal guide slot, the second longitudinal guide slot having a slot width narrower than the first mentioned longitudinal guide slot; and wherein the stop member has portions of varying width, a first portion having a width slidable in the first mentioned longitudinal guide slot but not slidable in the second longitudinal guide slot, and a second portion slidable in the second longitudinal guide slot, the stop member being selectively positionable to permit the second portion to be slidable in the second longitudinal guide slot.

8. The apparatus of claim 6 wherein the damping means comprises a fluidic damper having a rod and a fluid containing housing with the rod and the fluid containing housing being relatively movable under a dampening action, the rod being connected to one of the links and the fluid containing housing being connected to the other link.

9. The apparatus of claim 4 wherein the stopping means comprises a protrusion on an end portion of the sensor assembly, and wherein outward movement of the sensor assembly is stopped when the protrusion contacts an opposed stop surface in the coupling.

10. The apparatus of claim 1 wherein the damping means provides substantially less damping force for inward displacement of the sensor assembly into the fluid container than for outward displacement of the sensor assembly during removal from the fluid container.

11. An apparatus for removing and installing a sensor assembly through a valve attached to an opening in a process fluid container, the apparatus comprising:

a first support link pivotally joined to the sensor assembly;

a second support link pivotally joined to the first support link and pivotally joined to the valve, wherein the first support link and second support link are in a substantially collapsed condition when the sensor assembly is inserted through the valve and into the container and securely mounted relative to the container, and wherein the first and second support links are in an expanded condition when the sensor assembly is removed from the container and the valve;

a fluidic damper having a damping rod resistively movable relative to a housing as the sensor assembly is removed from the container and through the valve as the links expand, the damper connected between the support links wherein the rod is joined to one of the support links and the housing is joined to the other support link; and stopping means to stop movement of the sensor assembly at a selected position with respect to the valve so that the valve can be closed to seal the opening.

12. The apparatus of claim 11 wherein the stopping means is selectively releasable allowing continued movement of the sensor assembly beyond the selected position.

13. The apparatus of claim 12 wherein the stopping means comprises a control link having a longitudinal guide slot, and a stop member slidable in the longitudinal guide slot between ends thereof, wherein the first end of the control link is pivotally joined to one of the links and the stop member is mounted to the other link.

14. The apparatus of claim 13 wherein the control link includes a second longitudinal guide slot, providing an extension to the first mentioned longitudinal guide slot, having a slot width narrower than the first mentioned longitudinal guide slot; and wherein the stop member has portions of varying width, a first portion having a width slidable in the first mentioned longitudinal guide slot but not slidable in the second longitudinal guide slot, and a second portion slidable in the second longitudinal guide slot, the stop member being positionable to have the first portion slidable in the first mentioned longitudinal guide slot and selectable to release the first portion from the first mentioned longitudinal guide slot and permit the second portion to slide in the second longitudinal guide slot.

15. The apparatus of claim 12 wherein the stopping means comprises a protrusion on an end portion of the sensor assembly, and wherein outward movement of the sensor assembly is stopped when the protrusion contacts an opposed stop surface at the selected position.

* * * * *

UNITED STATES PATENT AND TRADEMARK OFFICE

CERTIFICATE OF CORRECTION

PATENT NO. : 5,174,325

DATED : December 29, 1992

INVENTOR(S) : MARK C. OKEL, BARRY R. WEST

It is certified that error appears in the above-identified patent and that said Letters Patent is hereby corrected as shown below:

Col. 1, line 29, delete "unitare", insert --unit are--

Col. 3, line 23, delete "end", insert --ends--

Col. 4, lines 47-48, delete "assembly 1?", insert --assembly 10--

Signed and Sealed this

Second Day of November, 1993

Attest:

BRUCE LEHMAN

Attesting Officer

*Commissioner of Patents and Trademarks*